US012789408B2

(12) United States Patent
Ritzberger et al.

(10) Patent No.: US 12,789,408 B2
(45) Date of Patent: Nov. 10, 2026

(54) PROCESS AND SLIP FOR THE PRODUCTION OF CERAMIC SHAPED BODIES MADE OF ZIRCONIUM OXIDE BY 3D INKJET PRINTING

(71) Applicant: Ivoclar Vivadent AG, Schaan (LI)

(72) Inventors: Christian Ritzberger, Grabs (CH); Johannes Renner, Ostermundingen (CH)

(73) Assignee: Ivoclar Vivadent AG, Schaan (LI)

( * ) Notice: Subject to any disclaimer, the term of this patent is extended or adjusted under 35 U.S.C. 154(b) by 120 days.

(21) Appl. No.: 18/896,300

(22) Filed: Sep. 25, 2024

(65) Prior Publication Data

US 2025/0018599 A1 Jan. 16, 2025

Related U.S. Application Data

(60) Continuation of application No. 18/346,536, filed on Jul. 3, 2023, now Pat. No. 12,179,383, which is a division of application No. 16/660,156, filed on Oct. 22, 2019, now Pat. No. 11,738,478.

(30) Foreign Application Priority Data

Nov. 29, 2018 (EP) .................................... 18209271

(51) Int. Cl.

| | |
|---|---|
| ***B33Y 10/00*** | (2015.01) |
| ***A61K 6/818*** | (2020.01) |
| ***B28B 1/00*** | (2006.01) |
| ***C04B 35/119*** | (2006.01) |
| ***C04B 35/488*** | (2006.01) |
| *B33Y 70/00* | (2020.01) |
| *B33Y 80/00* | (2015.01) |

(52) U.S. Cl.

CPC .............. *B28B 1/001* (2013.01); *A61K 6/818* (2020.01); *C04B 35/119* (2013.01); *C04B 35/488* (2013.01); *B33Y 10/00* (2014.12); *B33Y 70/00* (2014.12); *B33Y 80/00* (2014.12); *C04B 2235/3206* (2013.01); *C04B 2235/3208* (2013.01); *C04B 2235/3225* (2013.01); *C04B 2235/3227* (2013.01); *C04B 2235/3229* (2013.01); *C04B 2235/3244* (2013.01); *C04B 2235/5454* (2013.01); *C04B 2235/6567* (2013.01); *C04B 2235/665* (2013.01)

(58) Field of Classification Search

None

See application file for complete search history.

(56) References Cited

U.S. PATENT DOCUMENTS

| | | | |
|---|---|---|---|
| 7,176,253 | B2 | 2/2007 | Xu et al. |
| 7,399,796 | B2 | 7/2008 | Xu et al. |
| 8,133,831 | B2 | 3/2012 | Laubersheimer et al. |
| 8,329,296 | B2 | 12/2012 | Apel et al. |
| 8,409,655 | B2 | 4/2013 | Uibel |
| 8,460,451 | B2 | 6/2013 | Xu et al. |
| 9,138,981 | B1 | 9/2015 | Hirsch et al. |
| 9,534,103 | B2 | 1/2017 | Xu et al. |
| 9,820,917 | B1 | 11/2017 | Xu et al. |
| 2004/0075197 | A1 | 4/2004 | Tang |
| 2010/0025874 | A1* | 2/2010 | Apel ..................... A61K 6/824 501/103 |
| 2012/0308837 | A1 | 12/2012 | Schlechtriemen et al. |
| 2013/0313738 | A1 | 11/2013 | Carden |
| 2014/0109797 | A1 | 4/2014 | Carden |
| 2016/0229128 | A1 | 8/2016 | Dayagi et al. |
| 2017/0326645 | A1 | 11/2017 | Saito et al. |
| 2018/0141235 | A1 | 5/2018 | Guenster et al. |
| 2018/0170812 | A1 | 6/2018 | Xu et al. |
| 2019/0231650 | A1 | 8/2019 | Yang et al. |

FOREIGN PATENT DOCUMENTS

| | | | |
|---|---|---|---|
| DE | 10115818 | A1 | 10/2002 |
| DE | 102012200654 | B4 | 1/2015 |

OTHER PUBLICATIONS

J. Ebert et al.: Direct Inkjet Printing of Dental Prostheses Made of Zirconia, J. Dent Res 88(7): 673-676, 2009 (Year: 2009).*

Test Report of Christian Ritzberger regarding EP 3659547, Jan. 5, 2023.

Manufacturer's brochure for the Ricoh MH5421F print head, Apr. 2017.

Press release from Xaar; "Xaar Introduces Latest Performance-Enhancing Printhead Technology for 3D Print," Sep. 12, 2018.

Zapka (editor), Inkjet Prining in Industry: Material, Technologies, Systems, and Applications, Wiley 2022.

F. Raether, A. Klimera, "Methods of Measurement and Strategies for Binder Removal in Ceramics," Ber. DKG 85 (2008) No. 13, 5-11.

B. Hartkopp et al, "Novel Piezo Inkjet Technology and Printhead Capable of Jetting Extreme Viscosity Fluids for Additive Manufacturing," Printing for Fabrication, 2021.

M. Molitch-Hou, "Quantica Disrupts Inkjet 3D Printing High-Performance, Multi-Material System," Nov. 2021.

M. Molitch-Hou, "Startup Accelerator: Quanitca Disrupts Inkjet 3D Printing with JetPack Development Platform," May 2022.

N. Jackson, M. Seal, "Pushing the boundaries of inkjet technology with high viscosity printing," Xaar plc, Nov. 2021.

R. Bernasconi et al, "Piezoelectric Drop-On-Demand Inkjet Printing of High•Viscosity Inks," Adv. Eng. Mater. 2021, pp. 1-14.

Opposition documents related to EP 3659547, Mar. 13, 2025.

(Continued)

*Primary Examiner* — Mohammad M Ameen

(74) *Attorney, Agent, or Firm* — Ann M. Knab; Thad McMurray

(57) ABSTRACT

Process and slip for the production of ceramic shaped parts made of zirconium oxide ceramic by a 3D inkjet printing process. The slip contains zirconium oxide which is suspended in a liquid medium, wherein the slip has a zirconium oxide content of from 68 to 88 wt.-% and contains not more than 5 wt.-% organic components. The process for the production of ceramic components comprises the layered shaping and subsequent sintering of the desired component from the slip.

9 Claims, No Drawings

(56) References Cited

OTHER PUBLICATIONS

Derby, B., Additive Manufacture of Ceramics Components by Inkjet Printing, 3D Printing—Review, Mar. 2015, vol. 1, No. 1, pp. 113-123.
Özkol, E., et al., Potentials of the "Direct inkjet printing" method for manufacturing 3Y-TZP based dental restorations, Journal of the European Ceramic Society, Mar. 19, 2012, vol. 32, No. 10, pp. 2193-2201.
Tosoh Corporation, Tosoh Zirconia Powder Specification and Typical Properties Zpex, 2011, 9 pages.
Özkol, E., Evaluation of the direct inkjet printing method for the fabrication of three-dimensional ceramic components, Doctoral Thesis at Rheinisch-Westfalischen Technischen Hochschule Aachen, Sep. 24, 2012, 187 pages.
Ebert, J., et al., Direct Inkjet Printing of Dental Prostheses Made of Zirconia, J. Dent. Res., 2009, vol. 88, No. 7, pp. 673-676.
Gebhardt, A., Vision Rapid Prototyping, Generative Manufacturing of Ceramic Parts—A Survey, Plenary Lecture of the DKG-Symposium, Nov. 29, 2005, vol. 83, No. 13, pp. 7-12.

* cited by examiner

PROCESS AND SLIP FOR THE PRODUCTION OF CERAMIC SHAPED BODIES MADE OF ZIRCONIUM OXIDE BY 3D INKJET PRINTING

CROSS-REFERENCE TO RELATED APPLICATIONS

This application is a continuation application of and claims priority to U.S. application Ser. No. 18/346,536, filed on Jul. 3, 2023, which is a divisional application of and claims priority to U.S. application Ser. No. 16/660,156, filed on Oct. 22, 2019, now U.S. Pat. No. 11,738,478, which claims priority to European Patent Application No. 18209271.8 filed on Nov. 29, 2018, all the disclosures of which are incorporated herein by reference in their entirety.

TECHNICAL FIELD

The present invention relates to a process and a slip for the production of ceramic shaped parts made of zirconium oxide ceramic, in particular dental restorations, by a 3D inkjet printing process.

BACKGROUND

So-called constructive methods are increasingly used to produce shaped bodies. The terms "rapid prototyping", "generative manufacturing processes" or "additive manufacturing processes" are often used as synonyms for these constructive methods. These terms combine different processes in which 3-dimensional models or components are produced from computer-aided design data (CAD data) (A. Gebhardt, Vision of Rapid Prototyping, Ber. DGK 83 (2006) 7-12). Examples of typical additive manufacturing processes are stereolithography, 3D printing and inkjet modelling. The principle of rapid prototyping is based on the layered construction of a three-dimensional component.

Among the 3D inkjet printing processes polymerizable ink printing is one of several processes. In addition, the printing of a binder in a powder bed or the printing of liquid waxes is also known. In the case of 3D inkjet printing processes, following the same principle as the standard inkjet printers known from everyday office life, 3D objects are printed directly in that polymerizable modelling materials ("inks") are dispensed in defined droplets through a piezo printhead which can have several nozzles, the ink is cured and a layer with the desired printed contour is thus formed.

In inkjet printing, piezo printheads can be used which have an ink inlet and a plurality of nozzles connected to the ink inlet, wherein a piezo element is allocated to each nozzle. The piezo elements of the individual nozzles can be actuated separately by a control unit. By applying control signals to the piezo elements, the piezo elements are deformed in a targeted manner in order to discharge a discrete droplet of the ink through the nozzle with defined droplet size as a result of the deformation. The size and volume of the droplets as well as the droplet sequence from the nozzle can be controlled by the applied electrical pulses. The operating frequency of a piezo element generally ranges up to approximately 20 kHz due to the geometry of the printhead and the rheology of the inks. The sum of the droplets on a substrate yields the desired defined two-dimensional structure.

The nozzles of such a printhead typically have a very small opening which lies in the size range of from 10 to 100 μm, for which reason the discharged droplets are consequently very small; their diameter corresponds in the first approximation to the opening of the nozzle, their volume lies in the picolitre range ($10^{-10}$ to $10^{-12}$ litres). It is therefore possible in such printing processes to print very fine structures in high resolution. In the case of 3D inkjet printing, low-viscosity, polymerizable, usually photopolymerizable substances are customarily used as inks, which are cured directly after the droplets strike the substrate. Typically this is done by moving one or more printheads across a substrate which print a two-dimensional structure consisting of a plurality of juxtaposed droplets, of a polymerizable ink comprising a photoinitiator, and subsequently (or in parallel) exposing the droplets with a light source which emits light with a suitable wavelength in order to polymerize the photopolymerizable material of the ink.

Usually, inks for such 3D inkjet printing processes contain fillers. Fillers can for example be pigments, opacifiers etc. which alter the optical properties of the ink. However, the flow properties of the ink can also be influenced or the rheology controlled by fillers. In the case of 3D inkjet printing, for the construction of ceramic shaped bodies filler particles are necessary. In this case, the filler particles are the actual construction material (e.g. oxide ceramic). The liquid surrounding them is merely the matrix for building up these particles into a shaped body using the described technique. The particles do not directly influence the aspect ratios (thicknesses or layer depths), but rather the mechanical, optical, thermal and electrical properties of the shaped body.

If it is desired to produce 3D shaped bodies from a specific material, such as for example metal or ceramic, filler particles are not simply auxiliary materials to set specific dimensions or mechanical properties of the shaped body, but an essential constituent of the ink, and the liquid constituents of the ink function as a type of carrier substance. As a first approximation the dimensions and mechanical properties of the three-dimensional shaped body are more easily achievable the higher the proportion of solids in the suspension is, i.e. the more particles are contained in the ink as fillers. Typically, the particle sizes lie in the range of from 0.1 to 1 μm, which are suitable in particular for achieving a high filler loading. However, a high proportion of solid particles can have a negative effect in two ways on the ink or subsequently on the droplet discharge/printing process. For one thing, the viscosity of the ink increases with increasing filler loading, and thus the flow properties of the ink deteriorate. For another, there is the risk that the fine nozzles become blocked or partially clogged, as a result of which the droplet discharge can be prevented or impeded.

Ceramic-filled inks, so-called slips, which are suitable for building up dental restorations and which can be used in the 3D inkjet printing processes according to the present invention are described in EP 2 233 449 A1 and corresponding U.S. Pat. No. 8,133,831, which is hereby incorporated by reference. These inks can contain ceramic particles, wax and at least one radically polymerizable monomer. Reference is made to the named published patent application for further details of these materials.

A process for the production of ceramic shaped parts by three-dimensional printing in which at least two ceramic slips with different compositions are used is known from EP 2 529 694 A1 and corresponding US2012308837, which is hereby incorporated by reference. The application of the ceramic slips is carried out in that the relative proportions of the slips are controlled depending on position such that they vary in predetermined manner within a layer along at least one direction in the layer plane, wherein the application pattern of the slips can vary from layer to layer. In this way, shaped bodies can be produced the material properties of which vary in three spatial directions.

WO 2015/056230 A1 and corresponding US2016229128, US2016236372, and US2016243619, which US published applications are hereby incorporated by reference, disclose a process for the production of three-dimensional objects by printing a slip which contains a carrier liquid and a dispersant. The temperature of the last-printed layer is set such that it lies above the boiling point of the carrier liquid and below the boiling point of the dispersant. In this way, the carrier liquid is already evaporated during the printing process, whereas at least part of the dispersant remains in the printed layer and holds the particles of the slip together.

The unsintered bodies obtained by layered construction are called green bodies or green compacts. A disadvantage of the known processes is that these green bodies must be debound in an additional step after the printing process before they can finally be sintered. During debinding, the organic constituents of the inks are largely removed by thermal decomposition. As a result of the decomposition of the organic constituents, the shaped bodies are exposed to high stresses which can lead to the formation of microcracks which impair the usage properties of the bodies or even make them completely unusable.

SUMMARY

The object of the invention is to overcome the disadvantages of the state of the art and to provide slips and processes for the production of ceramic bodies made of zirconium oxide ceramic by 3D printing, which make a separate debinding step superfluous.

DETAILED DESCRIPTION

The object is achieved by slips which contain zirconium oxide that is suspended in a liquid medium. The slip has a zirconium oxide content of from 68 to 88 wt.-%, preferably 70 to 86 wt.-% and particularly preferably 75 to 85 wt.-%. The slip is characterized in that it contains not more than 5 wt.-%, preferably not more than 3 wt.-%, more preferably not more than 2 wt.-% and most preferably not more than 1 wt.-% organic components, relative to the quantity of solid in the slip. The slip is also called suspension in the following.

The object according to the invention is furthermore achieved by a process for the production of ceramic components in which (i) the slip is shaped in layers into the geometric shape of the desired component, wherein the individual layers are each preferably dried after printing, (ii) the thus-obtained green compact is then optionally dried and (iii) the green compact is then optionally sintered.

The construction of the green compact in step (i) is preferably effected by a layered inkjet printing process. The later sintering shrinkage is to be borne in mind in the dimensioning of the component. According to a preferred embodiment of the process, the individual layers are each dried after printing. The drying of the layers is preferably effected with an airflow and/or by IR radiation.

In step (ii), the green compact obtained in step (i) is preferably (further) dried, wherein a certain amount of residual moisture may remain after drying. The aim of the drying is to solidify the previously liquid slip.

In particular, the invention relates to a process for the layered construction of a shaped body by means of a 3D inkjet printing process with a piezo printhead which has an ink inlet and several nozzles connected thereto to each of which is allocated a piezo element which can act on the associated nozzle in order to discharge ink from it, wherein each piezo element of the piezo printhead can be actuated individually by a control unit to discharge ink and its discharge is monitored by the control unit, wherein in the process the piezo printhead, controlled by the control unit, is moved over a construction area, the piezo elements are actuated individually by the control unit for the locally selective application of filled ink in order to thus apply a layer with the contour predetermined by the control unit, the applied layer is allowed to cure and the desired shaped body is built-up through successive application of layers each with the predetermined contour.

The control unit is preferably configured to move the piezo printhead out of the construction area after a predetermined number of printed layers and/or if the control unit detects a reduced discharge of ink in a nozzle of the piezo printhead, to then subject the nozzle or nozzles with reduced discharge or all nozzles of the piezo printhead to a nozzle cleaning by exciting the piezo element or elements of the nozzles to be cleaned with a frequency of at least 20 kHz to produce ultrasound waves in order to comminute and release any deposits in the nozzle.

The invention also relates to the use of the slip for the production of ceramic shaped parts.

The slip according to the invention and the process according to the invention are suitable for the production of ceramic components made of zirconium oxide ceramic, in particular for the production of dental restorations, such as e.g. an inlay, onlay, veneer, a crown, bridge, a framework, implant, a shell or an abutment.

However, the slip and the process are also suitable for the production of other medical prostheses such as hip or knee prostheses and orthopaedic bone substitute.

Moreover, the slip and the process are suitable for the production of complex ceramic components for machine building.

The zirconium oxide in the suspension is present in particulate form and has preferably a particle size of from 50 to 250 nm, more preferably from 60 to 250 nm and most preferably 80 to 250 nm, measured as the $d_{50}$ value, relative to the volume of all particles. The determination of the particle size is preferably effected with the static laser scattering (SLS) process according to ISO 13320:2009, e.g. using an LA-960 particle size analyzer from Horiba, or with the dynamic light scattering (DLS) process according to ISO 22412:2017, e.g. using a NANO-flex particle measurement device from Colloid Metrix. $d_{50}$ means that 50% of the particles are smaller and 50% of the particles are larger than the cited value.

The ceramic particles should be much smaller than the average diameter of the nozzle of the printhead of the inkjet printer used with which the slip is printed. In order to enable printing with current inkjet printers which have a nozzle diameter of approximately 100 μm or less, ceramic particles with a maximum particle size of less than or equal to 5 μm, in particular less than or equal to 1 μm are preferably used in the slip according to the invention. The particles preferably have a size of from 0.01 to 5 μm, particularly preferably from 0.01 to 2 μm and quite particularly preferably from 0.01 to 1 μm, wherein the absolute upper and lower limits of the size of the ceramic particles are meant here.

The primary particle size of the zirconium oxide lies in particular in the range of from 30 to 100 nm and it is usually likewise determined with a dynamic light scattering (DLS) process as described above or by means of scanning electron microscopy.

The zirconium oxide is, in particular, zirconium oxide based on tetragonal zirconia polycrystal (TZP). Zirconium oxide which is stabilized with $Y_2O_3$, $La_2O_3$, $CeO_2$, MgO and/or CaO and in particular is stabilized with 2 to 14 mol.-%, preferably with 2 to 10 mol.-% and more preferably 2 to 8 mol.-% and most preferably 3 to 6 mol.-% of these oxides, relative to the zirconium oxide content is preferred.

The zirconium oxide used in the process according to the invention can also be stained. The desired staining is achieved preferably by adding one or more colouring elements to the zirconium oxide. The addition of colouring elements is sometimes also called doping and it is usually effected during the production of the zirconium oxide powder by co-precipitation and subsequent calcining. Examples of suitable colouring elements are Fe, Mn, Cr, Ni, Co, Pr, Ce, Eu, Gd, Nd, Yb, Tb, Er and Bi.

The zirconium oxide in the suspension can also be a mixture of zirconium oxide powders with different compositions, leading in particular to a different colouring and/or translucence in the dental restoration ultimately produced. With the aid of a mixture of differently coloured zirconium oxide powders, the desired colour for the desired shaped body can thus be set easily and in a targeted manner. In the same way, the translucence of the shaped body produced can also be set in a targeted manner through the use of a mixture of zirconium oxide powders with different translucence. The degree of translucence of the produced shaped body can be controlled in particular through the yttrium oxide content of the zirconium oxide powders used.

The suspension can also be a mixture of different suspensions with, for example, differently coloured zirconium oxide, wherein the different suspensions can be mixed with each other before printing or during the printing process. A mixing during the printing process can be effected for example by printing two or more different suspensions simultaneously but each with separate printheads.

In the process according to the invention the zirconium oxide is present as a suspension in a liquid medium. The liquid medium can contain organic and/or inorganic solvents. A preferred inorganic solvent is water. Preferred organic solvents are solvents miscible with water, in particular alcohols, ketones, esters, ethers and mixtures thereof. Mixtures of water with one or more organic solvents can likewise be used. In particular, the liquid medium contains water, wherein those suspensions which contain exclusively water as solvent are quite particularly preferred.

The slips according to the invention are characterized in that the slip has only small quantities of organic components, i.e. it contains organic components in a quantity of not more than 5 wt.-%, preferably not more than 3 wt.-%, more preferably not more than 2 wt.-% and most preferably not more than 1 wt.-%, relative to the quantity of solid in the suspension.

In a further preferred embodiment the liquid medium contains organic components in a quantity of from 0.05 to 5 wt.-%, in particular 0.1 to 3 wt.-%, more preferably 0.1 to 2 wt.-% and most preferably 0.1 to 1 wt.-%, relative to the quantity of solid in the suspension.

In particular dispersants, binders, agents for setting the pH, stabilizers and/or defoamers come into consideration as organic components.

The dispersant serves to prevent the agglomeration of suspended particles to form larger particles. The quantity of dispersant in the slip is in preferably 0.01 to 5 wt.-%, more preferably 0.1 to 2 wt.-% and most preferably 0.1 to 1 wt.-%, relative to the quantity of solid in the suspension.

Suitable dispersants are water-soluble polymers such as polyvinyl alcohols, polyethyleneimines, polyacrylamides, polyethylene oxides, polyethylene glycols, homo- and copolymers of (meth)acrylic acid, polyvinylpyrrolidone, biopolymers, such as starches, alginates, gelatins, cellulose ethers, such as carboxymethyl cellulose, vinylsulfonic acid and vinylphosphonic acid.

Preferred dispersants are amino alcohols, such as ethanolamine, glycols such as ethylene glycol and dipropylene glycol, carboxylic acids, such as maleic acid and citric acid, and carboxylic acid salts, as well as mixtures of these dispersants.

It is further preferred that the slip contains as dispersant at least one compound selected from amino alcohol, glycol, carboxylic acid and carboxylic acid salt. The slip particularly preferably contains at least one compound selected from ethanolamine, ethylene glycol, dipropylene glycol, citric acid and citric acid salt.

Particularly preferred dispersants are polycarboxylic acids, carboxylic acids, polycarboxylates, carboxylates and/or amines. Quite particularly preferred are citric acid, acetic acid, maleic acid, ammonium citrate, diammonium citrate, triammonium citrate, ammonium maleate, diammonium maleate and ammonium formate.

Quite particularly preferred amines are ethanolamine, diethanolamine and triethanolamine.

The binder promotes the cohesion of particles in the green body present after step (i). The quantity of binder in the slip is preferably 0.01 to 5 wt.-%, more preferably 0.01 to 3 wt.-% and most preferably 0.01 to 2 wt.-%, relative to the quantity of solid in the suspension.

Examples of suitable binders are methylcellulose, sodium carboxymethyl cellulose, starches, dextrins, sodium alginate, ammonium alginate, polyethylene glycols, polyvinyl butyral, acrylate polymers, polyethyleneimine, polyvinyl alcohol, polyvinylpyrrolidone and mixtures thereof.

Preferred binders are polyvinyl alcohol, polyvinyl acetate, polyvinylpyrrolidone, polyacrylic acid, copolymers of acrylic acid ester and acrylic acid, polyethyl acrylate, polymethacrylic acid, polymethyl methacrylate, ammonium polyacrylate, ammonium polymethacrylate, polyethylene glycol and solid copolymers of ethylene glycol and propylene glycol.

Particularly preferred binders are polyglycols and glycols, quite particularly preferably dipropylene glycol and/or polyethylene glycol.

It is a further advantage of the green compact obtainable through the process according to the invention that, despite small proportions of binder, it has sufficient strength even without prior presintering to be able to be processed further.

Acids and bases, such as carboxylic acids, e.g. 2-(2-methoxyethoxy)acetic acid and 2-[2-(2-methoxyethoxy) ethoxy] acetic acid, inorganic acids, e. g. hydrochloric acid and nitric acid, as well as ammonium hydroxide and tetramethylammonium hydroxide, are preferred as agents for setting the pH and as stabilizers. It is particularly preferred that the liquid medium contains tetramethylammonium hydroxide.

Preferred agents for setting the pH are acids, bases and salts thereof. Quite particularly preferred are $HNO_3$, HCl, $NH_4OH$, 2,2-methoxyethoxy citric acid, 2,2,2-methoxyethoxyethoxy citric acid and/or tetramethylammonium hydroxide.

The defoamer serves to prevent air bubbles in the suspension. It is typically used in the liquid medium in a quantity of from 0.00001 to 1 wt.-%, preferably 0.00001 to 0.5 wt.-% and particularly preferably 0.001 to 0.1 wt.-%, relative to the quantity of solid in the suspension. Examples of suitable defoamers are paraffin, silicone oils, alkyl polysiloxanes, higher alcohols, propylene glycol, ethylene oxide-propylene oxide adducts and in particular alkyl polyalkylene glycol ether.

It is further preferred that the suspension has a viscosity of from 5 mPas to 500 mPas, preferably 5 mPas to 250 mPas and particularly preferably 5 to 100 mPas. Unless otherwise indicated, the viscosity is measured with a rotational viscometer with cone and plate system, diameter 50 mm and angle 1° (Modular Compact Rheometer MCR302, from Anton Paar GmbH), at a shear rate in the range of from 0.1-1000 $s^{-1}$ and a temperature of 25° C.

To produce the suspension the zirconium oxide is typically intimately mixed with the liquid medium in powder form. Mixtures of for example differently coloured zirconium oxide can also be used. During this mixing, agglomerates present are usually also broken up and the zirconium oxide used can also be ground in order to produce the desired particle size. The mixing of zirconium oxide and liquid medium can therefore be carried out advantageously in agitator bead mills, for example.

However, agglomerates of ceramic primary particles can also be present in the slip provided they are small enough to be able to be printed with the desired inkjet nozzles, i.e. in preferred embodiments the agglomerates as a whole satisfy the above particle size conditions. However, it is preferred that the particles are present in non-agglomerated form, for example wholly or predominantly in the form of primary particles.

The slips according to the invention preferably contain:

60 to 90 wt.-% zirconium oxide particles, 10 to 40 wt.-% liquid medium, preferably water, 0.002 to 2.0 wt.-% dispersant, 0.001 to 2.0 wt.-% binder and 0.001 to 1.0 wt.-% agent for setting the pH in each case relative to the total mass of the slip.

Slips with the following composition are particularly preferred (relative to the total mass of the slip):

| [wt.-%] | Constituent |
|---|---|
| 10-40 | water |
| 60-90 | $ZrO_2$ particles |
| 0.001-1.0 | polycarboxylic acid, carboxylic acid, polycarboxylate and/or carboxylate (dispersant) |
| 0.001-1.0 | amine (dispersant) |
| 0.001-2.0 | polyglycol and/or glycol (binder) |
| 0.001-1.0 | acid, base or a salt thereof (agent for setting the pH) |

Slips with the following composition are more preferred (relative to the total mass of the slip):

| [wt.-%] | Constituent |
|---|---|
| 15-35 | water |
| 65-85 | $ZrO_2$ particles |
| 0.001-0.5 | polycarboxylic acid, carboxylic acid, polycarboxylate and/or carboxylate (dispersant) |
| 0.001-0.5 | amine (dispersant) |
| 0.01-2.0 | polyglycol and/or glycol (binder) |
| 0.01-1.0 | acid, base or a salt thereof (agent for setting the pH) |

Slips with the following composition are most preferred (relative to the total mass of the slip):

| [wt.-%] | Constituent |
|---|---|
| 15-30 | water |
| 70-85 | $ZrO_2$ particles |
| 0.01-0.5 | polycarboxylic acid, carboxylic acid, polycarboxylate and/or carboxylate (dispersant) |
| 0.001-0.5 | amine (dispersant) |
| 0.1-2.0 | polyglycol and/or glycol (binder) |
| 0.01-1.0 | acid, base or a salt thereof (agent for setting the pH) |

Slips which contain the preferred and particularly preferred constituents defined above are preferred in all cases.

The slips according to the present invention are particularly suitable for use in inkjet printing, in principle however they can also be used in other processes, for instance a green body can also be produced from the slip according to the invention using a different additive manufacturing process, such as for instance by stereolithography, or by the hot-casting process (low-pressure injection moulding) or by a drop-on-powder process (printing in a powder bed). In the drop-on-powder process the slip is preferably printed in a bed of Zro: particles.

Preferably, a green body is produced from the slip according to the invention by forming the slip layer by layer in an inkjet printing process into the geometric shape of the green body. Commercially available, high-resolution industrial multi-nozzle printheads are preferably used in the process according to the invention. To print several slips simultaneously, preferably printers are used with several printheads which are each supplied from different reservoirs so that two or more different slips can be printed.

To produce the green compact, a support material can be printed together with the ceramic slip. Support materials are materials which are used when printing undercuts, overhangs or cavities and which are removed from the body again after printing. The printing of the support material is preferably effected with a separate printhead. The support material preferably contains exclusively organic constituents which are completely removed during debinding and sintering. The binders used to produce the slip are particularly suitable as support materials. Preferred support materials are described in the following patents: U.S. Pat. Nos. 9,138,981 B2, 8,460,451 B2, 7,176,253 B2, 7,399,796 B2 and 9,534,103 B2, all of which are hereby incorporated by reference. Unlike the organic constituents present in the slip, the support materials can be relatively easily removed because they are not trapped in the ceramic material.

The unsintered bodies obtained by layered construction are called green bodies or green compacts. The green body is preferably dried. The drying can be effected in layers and/or in a separate process step (ii) after the completion of the green body, preferably with the help of an airflow and/or IR radiation. A layered drying and in particular a layered drying with subsequent drying of the green body are preferred.

The drying is preferably effected at a temperature of from 10 to 100° C., preferably 20 to 80° C. and more preferably from 20 to 60° C.

The drying is further preferably effected at a relative air humidity of 20 to 90%, preferably 30 to 90% and more preferably from 40 to 90%.

The duration of the drying is preferably 0.1 to 12 h, more preferably 0.1 to 6 h and most preferably 1 to 6 h.

The drying of the printed component or of the individual printed layers can be effected inside the printer or, in the case of the printed component, also in an climate chamber after the printing process. The drying can be effected in each case with or without convection, by means of infrared radiation and/or microwaves. According to a particularly preferred embodiment of the process according to the invention, the drying of the green body is effected as part of the sintering in step (iii).

The green body obtained after the drying is characterized by a surprisingly high density. The green body preferably has a density of from 3.3 to 4.0 g/cm$^3$, more preferably from 3.35 to 3.9 g/cm$^3$ and most preferably from 3.4 to 3.9 g/cm$^3$. The density is determined by means of mercury porosimetry according to ISO 15901-1:2016.

In a further preferred embodiment, the green body has a pore volume of from 0.08 to 0.14 cm$^3$/g, in particular 0.08 to 0.12 cm$^3$/g and more preferably 0.08 to 0.10 cm$^3$/g. The pore volume is determined by means of mercury porosimetry according to ISO 15901-1:2016.

In another preferred embodiment, the green body has a pore diameter of from 0.02 to 0.12 μm, in particular 0.03 to 0.10 μm and more preferably 0.04 to 0.08 μm, measured as the $d_{50}$ value relative to the volume of the particles. The pore diameter is determined by means of mercury porosimetry according to ISO 15901-1:2016.

After the drying, the green body can optionally be stained individually in a further step by applying a staining solution. The staining solution is preferably applied with the help of a spraying device, preferably a robot-controlled spraying device. With this individual colouring, the translucence and/or the colour can be set locally in a defined manner. The translucence is here set by solutions which preferably contain yttrium, lanthanum, gadolinium or Yb ions and mixtures thereof. The colour is set by solutions which contain Fe, Mn, Cr, Co, Ni, Ce, Pr, Tb, Bi, Er ions and mixtures thereof.

Because of its low content of organic components, the green body can be sintered directly after printing and optionally subsequent drying. A separate heat treatment to remove the organic constituents (debinding) is not required.

If the drying of the green body is to be effected in the course of sintering, the printed green body is preferably placed for this purpose on a suitable carrier in a sintering furnace with adjustable furnace hood. With an open furnace hood and at room temperature, the green body is placed in the furnace, then the heating elements located in the furnace hood are heated, preferably to a temperature of from 30 to 400° C. and the furnace hood is then slowly lowered. The sintering is effected once the furnace hood has closed the furnace. A drying of the green compact in the course of sintering comes into consideration in particular when the green compact has a residual moisture of less than 5 wt.-%.

The green bodies according to the invention are characterized in that they experience only a low linear shrinkage during the dense sintering. The production of dental restorations with precisely the desired dimensions is thereby made easier and the accuracy of fit thereof is improved.

It is preferred that the green bodies according to the invention have a linear shrinkage of less than 18%, more preferably less than 17% and most preferably less than 16%. The linear shrinkage S results from the following formula and, for the determination thereof, measurements are carried out by means of a Netzsch DIL402 Supreme dilatometer in a temperature range of from 20° C. to 1550° C. at a heating-up rate of 2 K/min on test pieces with the dimensions length=25 mm±1 mm, width=5 mm±0.5 mm and height=4 mm±0.5 mm.

$$\text{linear shrinkage: } S = \frac{\text{length untreated} - \text{sintered length}}{\text{length untreated}} * 100 \text{ in } \%$$

From the linear shrinkage S the volume shrinkage $S_{Vol}$ can be calculated according to the following formula:

$$\text{volume shrinkage: } S_{Vol} = \left[1 - \left(1 - \frac{\text{linear shrinkage}}{100}\right)^3\right] * 100 \text{ in } \%$$

The green bodies according to the invention are preferably densely sintered in step (iii) at a sintering temperature of from 1200 to 1600° C., more preferably 1300 to 1550° C., most preferably 1350 to 1500° C. The dense sintering results in the formation of a ceramic shaped body which preferably has a density of more than 5.9 g/cm$^3$, more preferably more than 6.00 g/cm$^3$ and most preferably more than 6.02 g/cm$^3$. The obtained shaped body has outstanding mechanical properties also because of this high density.

It is a particular advantage that the whole dense-sintering process with the heating up from room temperature, the holding at the maximum sintering temperature and the cooling down occupies only a very short period of time and, after the completion thereof, shaped bodies and in particular dental restorations with the sought high translucence and very good mechanical properties are nevertheless obtained. The process according to the invention is thus superior to conventional processes, which require a very long period of time in order to produce a dental restoration with comparable translucence by sintering. The process according to the invention thus combines the advantage of a very short process duration with that of the very good optical and mechanical properties of the dental restoration produced.

In a preferred embodiment of the process according to the invention, the period for heating up the green body from room temperature to sintering temperature for the dense sintering, holding at the sintering temperature and cooling down to the final temperature is not more than 6 hours, preferably not more than 4 hours and more preferably not more than 2 hours. By "final temperature" is meant here a temperature at which the sample can be picked up by hand, and it is in particular 15 to 80° C., preferably 25 to 60° C. and more preferably approximately 50° C. By "room temperature" is preferably meant a temperature of 15 to 30° C., more preferably 20 to 25° C. and most preferably approximately 25° C.

The heating-up rate is preferably more than 10 K/min, more preferably more than 20 K/min and most preferably more than 30 K/min. The holding time is preferably less than 120 min, more preferably less than 60 min and most preferably less than 30 min. The cooling rate from the sintering temperature to the final temperature is preferably more than 50 K/min, more preferably more than 100 K/min and most preferably more than 150 K/min.

Preferred ranges for the heating-up rate are 10 K/min to 500 K/min, more preferably 20 K/min to 300 K/min and most preferably 30 K/min to 200 K/min.

The holding times are preferably 1 minute to 60 minutes, more preferably 1 minute to 30 minutes and most preferably 1 minute to 10 minutes.

Preferred ranges for the cooling rate are 10 K/min to 500 K/min, more preferably 20 K/min to 300 K/min and most preferably 30 K/min to 200 K/min.

Through the low linear shrinkage which the shaped green body according to the invention experiences during the dense sintering, the production of dental restorations with precisely the desired dimensions is made easier and the accuracy of fit thereof is improved. It goes without saying that the shrinkage during sintering is to be taken into account accordingly during the printing process, i.e. the shaped bodies are printed scaled up so that they have the desired dimensions after the sintering.

In a preferred embodiment (a) the green body is heated up to a temperature $T_1$, (b) optionally further heated up to a temperature $T_2$ and held and sintered at the temperature $T_2$ and (c) cooled down to a temperature $T_3$, wherein the temperature $T_1$ is 0 to 500 K, preferably 10 to 250 K, more preferably 25 to 200 K and most preferably 50 to 100 K below the temperature $T_2$ and step (a) is effected at a lower pressure than step (b). Here it is further preferred that the pressure in step (a) is less than 200 mbar, preferably less than 100 mbar and more preferably less than 50 mbar, and is preferably in the range of from 0.1 to 200 mbar, more preferably 1 to 150 mbar and most preferably 50 to 100 mbar. It is likewise preferred that step (b) is effected at a pressure of more than 500 mbar and preferably at ambient pressure, and preferably in an oxygen-containing atmosphere such as air, oxygen-enriched air or oxygen. In a preferred embodiment, an oxygen-containing atmosphere, preferably air, oxygen-enriched air, or oxygen flows continuously through the heating chamber used for the heating up during step (b).

The shaped body obtained after the dense sintering can optionally also be provided with a veneer, polished and/or glazed.

The dental restoration produced using the process according to the invention is in particular a bridge, an inlay, an onlay, a crown, a veneer, an implant, a shell or an abutment.

The invention is explained in more detail in the following with reference to examples.

EXAMPLES

Example 1

Suspension with 76 wt.-% Zirconium Oxide 3.15 g of a dispersant containing citric acid or citric acid salt (Dolapix CE64, from Zschimmer & Schwarz) and 1.5 g tetramethylammonium hydroxide were dissolved one after the other in 194.4 g of distilled water. The solution had a pH of 10-10.5.

This solution was placed in the storage tank of a MicroCer agitator bead mill (from Netzsch), the grinding chamber and rotor of which were made of zirconium oxide. The grinding chamber was filled with 60 ml zirconium oxide grinding beads with a diameter of from 0.2-0.3 mm (from Tosoh). At a rotational speed of the rotor of 1500 rpm, the solution was continuously pumped through the grinding chamber using a peristaltic pump (tube internal diameter 8 mm). 630 g zirconium oxide powder which was partially stabilized with 3 mol.-% $Y_2O_3$ (TZ-PX-245 from TOSOH Corporation, primary particle size: 40 nm) was then added to the solution in the storage tank, continuously and with stirring. Once the addition of the zirconium oxide powder was completed the mixture obtained was pumped through the grinding chamber and back into the storage tank continuously for 45 min at a rate of approx. 40 l/h. The suspension prepared in this way was transferred into a plastic beaker and stirred very slowly by means of a magnetic stirrer in order to remove trapped air bubbles. In addition, one drop of an alkyl polyalkylene glycol ether was added as defoamer (Contraspum, from Zschimmer & Schwarz).

The suspension obtained had a zirconium oxide content of 76 wt.-%. The viscosity $\eta$ of the suspension was 7.25 mPas (at a shear rate of 500 $s^{-1}$ and a temperature of 25° C.).

Example 2

Production of Test Pieces by Means of 3D Inkjet Printing

An inkjet printhead (Ricoh MH5421F) with fluid circulation directly at the nozzles was used for the printing process. The printhead was operated with a constant positive pressure (from 30-120 mbar) at the supply end and with a constant negative pressure (from −40 to −150 mbar) at the return end. Test pieces with the following dimensions were printed with the slip from Example 1: length=25 mm±1 mm, width=5 mm±0.5 mm and height=4 mm±0.5 mm. The linear shrinkage was 15.43%. For measuring the density test pieces with the following dimensions were prepared: length=5 mm±1 mm, width=5 mm±1 mm and height=10 mm±1 mm. The test pieces were debound at 500° C. and then had a density of 3.678 g/cm³. The test pieces were then densely sintered in the sintering furnace (Programat CS4 from Ivoclar Vivadent AG) according to the following temperature schedule:

| | |
|---|---|
| approx. 25° C. to 900° C. | (6.7 min) |
| 900° C. to 1460° C. | (11.2 min) |
| 1460° C. to 1460° C. | (5.0 min) |
| 1460° C. to 1200° C. | (3.7 min) |
| 1200° C. to approx. 1000-950° C. | (45-50 s) (furnace opens) |
| 950° C.-1000° C. to approx. 50° C. | (7 min) |

Example 3

Suspension with 83 wt.-% Zirconium Oxide

For the preparation of a suspension with 83 wt.-% zirconium oxide and the processing thereof to form test pieces (A) and blocks for "chairside" application (B), Example 1 was repeated with the variation that the solution contained 164.5 g distilled water, 4.05 g dispersant containing citric acid or citric acid salt (Dolapix CE64, from Zschimmer & Schwarz) and 1.5 g tetramethylammonium hydroxide, and that 810 g zirconium oxide powder which was partially stabilized with 5 mol.-% $Y_2O_3$ (TZ-PX-430 from TOSOH Corporation, primary particle size: 90 nm) was added and the presintering was carried out at 900° C. for 2 h, wherein the heating-up rate was likewise 0.250 K/min.

The viscosity $\eta$ of the suspension was 7.0 mPas (at a shear rate of 1000 $s^{-1}$ and a temperature of 25° C.).

Example 4

Production of Test Pieces by Means of 3D Inkjet Printing

Test pieces were produced with the slip from Example 3 in the manner described in Example 2. The linear shrinkage was 14.43%. The test pieces (length=5 mm±1 mm, width=5 mm±1 mm and height=10 mm±1 mm) were debound at 500° C. and then had a density of 3.791 g/cm$^3$. The test pieces were then densely sintered in the sintering furnace (Programat CS4 from Ivoclar Vivadent AG) according to the temperature schedule described in Example 2.

Example 5

Suspension with 80 wt.-% Zirconium Oxide

For the preparation of a suspension with 80 wt.-% zirconium oxide and the processing thereof to form test pieces (A), Example 1 was repeated with the variation that the solution contained 179.5 g distilled water, 3.6 g dispersant containing citric acid or citric acid salt (Dolapix CE64, from Zschimmer & Schwarz) and 1.5 g tetramethylammonium hydroxide, and that 720 g zirconium oxide powder which was partially stabilized with 4.25 mol.-% $Y_2O_3$ (TZ-PX-551 from TOSOH Corporation, primary particle size: 90 nm) was added.

The viscosity η of the suspension was 14.6 mPas (at a shear rate of 500 s$^{-1}$ and a temperature of 25° C.).

Example 6

Production of Test Pieces by Means of 3D Inkjet Printing

Test pieces were produced with the slip from Example 5 in the manner described in Example 2. The linear shrinkage was 14.59%.

The test pieces were debound at 500° C. and then had a density: 3.780 g/cm$^3$.

Example 7

Suspension with 83 wt.-% Zirconium Oxide

For the preparation of a suspension with 83 wt.-% zirconium oxide and for the processing thereof to form test pieces (A), Example 1 was repeated with the variation that the solution contained 164.5 g distilled water, 3.15 g dispersant containing citric acid or citric acid salt (Dolapix CE64, from Zschimmer & Schwarz) and 1.5 g tetramethylammonium hydroxide, and that 810 g zirconium oxide powder which was partially stabilized with 3 mol.-% $Y_2O_3$ (TZ-PX-245 from TOSOH Corporation, primary particle size: 40 nm) was added.

Example 8

Production of Test Pieces by Means of 3D Inkjet Printing

Test pieces were produced with the slip from Example 7 in the manner described in Example 2. The test pieces were debound at 500° C. and then had the following properties:

pore volume: 0.1139 cm$^3$/g pore radius: 0.0190 μm density: 3.562 g/cm$^3$.

Example 9

Suspension with 83 wt.-% Zirconium Oxide

For the preparation of a suspension with 83 wt.-% zirconium oxide and the processing thereof to form test pieces (A), Example 1 was repeated with the variation that the solution contained 164.5 g distilled water, 3.15 g dispersant containing citric acid or citric acid salt (Dolapix CE64, from Zschimmer & Schwarz) and 2.0 g tetramethylammonium hydroxide, and that 810 g zirconium oxide powder which was partially stabilized with 4.25 mol.-% $Y_2O_3$ (TZ-PX-551 from TOSOH Corporation, primary particle size: 90 nm) was added.

Example 10

Production of Test Pieces by Means of 3D Inkjet Printing

Test pieces were produced with the slip from Example 9 in the manner described in Example 2. The test pieces were debound at 500° C. and then had the following properties:

pore volume: 0.1109 cm$^3$/g pore radius: 0.0248 μm density: 3.547 g/cm$^3$.

Example 11

Suspension with 83 wt.-% Zirconium Oxide

For the preparation of a suspension with 83 wt.-% zirconium oxide and the processing thereof to form test pieces (A), Example 1 was repeated with the variation that the solution contained 164.5 g distilled water, 3.15 g dispersant containing citric acid or citric acid salt (Dolapix CE64, from Zschimmer & Schwarz) and 2.0 g tetramethylammonium hydroxide, and that 810 g zirconium oxide powder which was partially stabilized with 5.0 mol.-8 $Y_2O_3$ (TZ-PX-430 from TOSOH Corporation, primary particle size: 90 nm) was added.

Example 12

Production of Test Pieces by Means of 3D Inkjet Printing

Test pieces were produced with the slip from Example 11 in the manner described in Example 2. The test pieces were debound at 500° C. and then had the following properties:

pore volume: 0.1056 cm$^3$/g pore radius: 0.0253 μm density: 3.783 g/cm$^3$.

The invention claimed is:

1. A process for the production of a ceramic shaped part by an inkjet printing process, comprising (i) shaping a slip in layers into a geometric shape of the desired ceramic shaped part, wherein the individual layers are each dried after printing to produce a green compact, (ii) optionally drying the green compact, (iii) applying a staining solution to the green body, and (iv) sintering the green compact, wherein the layered construction of the green compact in step (i) is effected by a layered inkjet printing process, wherein the slip comprises zirconium oxide with a particle size of from 50 to 250 nm, measured as the $d_{50}$ value and relative to the volume of the particles, suspended in a liquid medium, and has a zirconium oxide content of from 68 to 88 wt.-%, and not more than 3 wt.-% organic components, relative to the total mass of the slip, wherein the slip has a viscosity of 5 to 100 mPas, measured at a shear rate of from 0.1 to 1000 s$^{-1}$ and at a temperature of 25° C., and wherein the printed ceramic shaped part is sintered directly after printing and optionally subsequent drying without a separate debinding step.

2. The process according to claim 1, wherein the staining solution comprises yttrium, lanthanum, gadolinium or Yb ions or a mixture thereof.

3. The process according to claim 1, wherein the staining solution comprises Fe, Mn, Cr, Co, Ni, Ce, Pr, Tb, Bi, Er ions or a mixture thereof.

4. The process according to claim 1, wherein the green body formed in step (i) is dried in step (ii) at a temperature of from 10 to 100° C.

5. The process according to claim 1, wherein the green body has a density of from 3.3 to 4.0 g/cm$^3$, and/or a pore volume of from 0.08 to 0.14 cm$^3$/g and/or a pore diameter of from 0.02 to 0.12 μm measured as the $d_{50}$ value relative to the volume of the particles.

6. The process according to claim 1, wherein the green body is densely sintered at a sintering temperature of from 1200 to 1600° C.

7. The process according to claim 6, wherein a period for heating up the green body from room temperature to the sintering temperature, holding at the sintering temperature and cooling down to a final temperature is not more than 6 hours.

8. The process according to claim 6, wherein (a) the green body is heated up to a temperature $T_1$, (b) is optionally further heated up to a temperature $T_2$ and held and sintered at the temperature $T_2$ and (c) is cooled down to a temperature $T_3$, wherein the temperature $T_1$ is 0 to 500 K below the temperature $T_2$ and step (a) is effected at a lower pressure than step (b).

9. The process according to claim 1, wherein the ceramic shaped part is a dental restoration comprising an inlay, onlay, veneer, a crown, bridge, a framework, an implant, a shell or an abutment.

* * * * *